(12) United States Patent
Zimmermann et al.

(10) Patent No.: US 8,563,082 B2
(45) Date of Patent: Oct. 22, 2013

(54) METHOD FOR PRODUCING A CROSS-LINKED SUBSTANCE, ESPECIALLY IN THE FORM OF A MICROCAPSULE OR LAYER

(75) Inventors: Ulrich Zimmermann, Waldbrunn (DE); Heiko Zimmermann, St. Ingbert (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 481 days.

(21) Appl. No.: 12/504,230

(22) Filed: Jul. 16, 2009

(65) Prior Publication Data

US 2009/0297595 A1  Dec. 3, 2009

Related U.S. Application Data

(62) Division of application No. 10/503,279, filed as application No. PCT/EP03/00952 on Jan. 30, 2003, now abandoned.

(30) Foreign Application Priority Data

Jan. 30, 2002 (DE) .................. 102 03 629

(51) Int. Cl.
*A61K 9/48* (2006.01)
*C07H 1/00* (2006.01)

(52) U.S. Cl.
USPC ........ 427/213.3; 424/451; 424/455; 424/93.7; 428/402; 428/402.2

(58) Field of Classification Search
USPC .............. 427/256, 389.9, 213.3–213.36, 483; 428/402–402.24, 407, 403, 423.1, 428/474.4; 521/57, 56, 76, 142; 536/123.1, 536/121; 424/450, 451, 455, 93.7, 184.1, 424/497, 489, 501, 490, 491, 492, 493, 494, 424/495; 514/772.4, 772.5, 781, 777, 779; 264/534, 4–4.7
See application file for complete search history.

(56) References Cited

U.S. PATENT DOCUMENTS 3,876,572 A  4/1975  Sliwka et al.
4,450,877 A  5/1984  Walker et al.

(Continued)

FOREIGN PATENT DOCUMENTS

JP  56107082 A  8/1981
WO  WO93/14264  7/1993

OTHER PUBLICATIONS

Tomida, H., et al.; "Preparation of Theophylline-Loaded Calcium Alginate Gel Capsules and Evaluation of Their Drug Release Characteristics", Chemical and Pharmaceutical Bulletin, Tokyo, vol. 41; No. 12, 1993, pp. 2161-2165.

(Continued)

*Primary Examiner* — James J Seidleck
*Assistant Examiner* — S. Camilla Pourbohloul
(74) *Attorney, Agent, or Firm* — Drinker Biddle & Reath LLP

(57) ABSTRACT

A device for producing a crosslinked substance, e.g., of crosslinked microcapsules (1) of a crosslinkable capsule substance, in particular crosslinked alginates, is described, having a first dispensing device (2) for dispensing a jet of the crosslinkable capsule substance and a crosslinking device for applying a crosslinking agent to the capsule substance, whereby the crosslinking device has a second dispensing device (5) which directs a jet (9, 13) of the crosslinking agent at the jet or at a layer of the capsule substance.

21 Claims, 6 Drawing Sheets

(56) References Cited

U.S. PATENT DOCUMENTS

Figure 1:
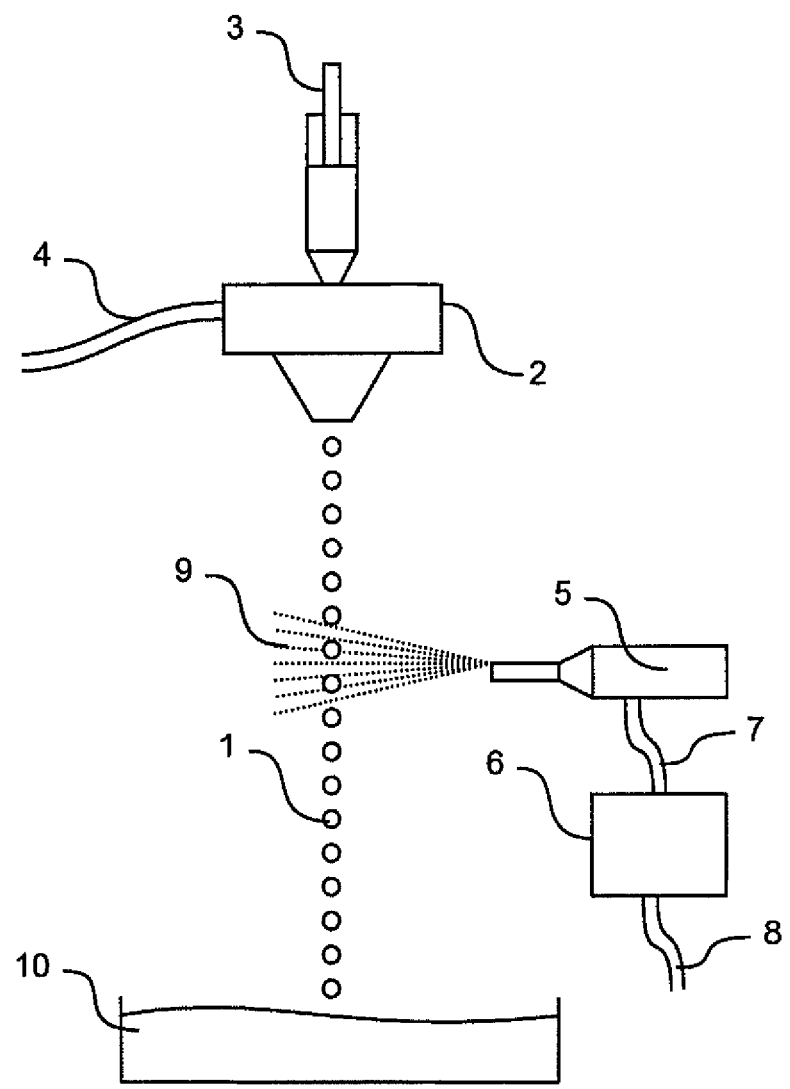

| | | | |
|---|---|---|---|
| 4,849,289 A | | 7/1989 | Bernard et al. |
| 5,246,636 A | | 9/1993 | Lew et al. |
| 5,595,757 A | * | 1/1997 | Kiefer et al. ............ 424/451 |
| 5,629,187 A | * | 5/1997 | Ors et al. ............... 435/178 |
| 5,656,469 A | | 8/1997 | Tresco et al. |
| 5,820,879 A | * | 10/1998 | Fernandez et al. ........ 424/450 |
| 5,851,453 A | | 12/1998 | Hanna et al. |
| 6,001,312 A | * | 12/1999 | Wang et al. ............. 422/131 |
| 6,066,575 A | | 5/2000 | Reardon et al. |
| 6,103,269 A | | 8/2000 | Wunderlich et al. |
| 6,465,226 B1 | | 10/2002 | Zimmermann |
| 2001/0024700 A1 | | 9/2001 | Shah et al. |
| 2002/0113224 A1 | | 8/2002 | Zimmermann |

OTHER PUBLICATIONS

Zimmermann, U., et al.; "Microencapsulation-Based Cell Therapy", Biotechnology, vol. 10, ISBN 3-527-28320-X.

Kuhtreiber, W.M.; Cell Encapsulation Technology and Therapeutics, Birkhauser Boston; $1^{st}$ Edition Jun. 1, 1999; ISBN 081764010X; printout from Internet with sample pages available at: http://www.amazon.com/gp/reader/081764010X/ref=sib_dp_pt/102-5705600-5970551#reader-link.

* cited by examiner

METHOD FOR PRODUCING A CROSS-LINKED SUBSTANCE, ESPECIALLY IN THE FORM OF A MICROCAPSULE OR LAYER

This is a divisional application of U.S. patent application Ser. No. 10/503,279, filed on Mar. 22, 2005, pending as of the filing of this application, which is a National Stage application of PCT International Application No. PCT/EP03/00952, filed on Jan. 30, 2003, which in turn claims the benefit of DE Application No. 10203629.2, filed on Jan. 30, 2002, each of which is hereby incorporated by reference in its entirety herein.

The invention relates to a device for producing a crosslinked substance, e.g., in the form of microcapsules or layers, in particular for biological or medical applications, having a first dispensing device for dispensing a jet of a crosslinkable substance and a crosslinking device for applying a crosslinking agent to the crosslinkable substance. This invention also relates to a method of producing the crosslinked substance. Furthermore, this invention relates to improved microcapsules or layers produced as crosslinked substance from a crosslinkable substance.

It is known from Ulrich Zimmerman et al., Microencapsulation-Based Cell Therapy, *Biotechnology*, volume 10, ISBN 3-527-28320-X that so-called microcapsules can be used for incorporation of medicinal active ingredients. Such microcapsules may be made of ionotropic gels, for example, which undergo crosslinking and curing due to application of ions and thus enclose the medicinal active ingredient to be administered. There is medicinal use of microcapsules in transplantation medicine, for example. Microcapsules are transplanted with an active ingredient (e.g., medicinal active substance, insulin-producing cells or tissue) into the patient to be treated (e.g., into the liver or intramuscularly). In the given example, without a coating, the patient's endogenous immune system would recognize and reject the foreign cells. This is advantageously prevented by enclosing the cells in the microcapsules. The foreign encapsulated cells are effectively separated from the endogenous immune system, whereas the shell of the microcapsules is permeable for the medicinal active ingredient contained or produced therein. Alginates, for example, are used as ionotropic gels in transplantation medicine.

The range of application of the traditional active ingredient encapsulation is limited because all encapsulation with biocompatible polymers has previously permitted only limited crosslinking densities and thus a relatively low reliability. With the traditional encapsulation in the case of encapsulation with alginates, for example, the permeability of the capsules can be reduced by increasing the alginate concentration, but this is also associated with an increased viscosity, which in turn limits the formation of the capsules.

A device for producing such microcapsules is also known from the publication cited in the beginning; with this device, a mixture of alginates and the medicinal active ingredients to be administered is dispensed through a nozzle, with air being blown through a coaxial nozzle arrangement with the jet emerging in order to promote the formation of small droplets of the mixture. The droplet jet produced in this way then falls into a precipitation bath with a crosslinking agent (e.g., a solution containing barium ions, calcium ions, iron ions or lanthanum ions), whereby the ions lead to crosslinking of the alginates and thus to formation of capsules.

One disadvantage of the known device is the fact that crosslinking of the alginate droplets in the precipitation bath starts from the surface of the alginate droplets and progresses inward. First a crosslinked layer is formed on the droplet surface, with the result that the divalent cations can no longer penetrate freely into the deeper regions of the droplets. As a result, non-homogeneous crosslinking of the microcapsules may occur. There may be instabilities in the microcapsules, leading to extremely fine cracks in subsequent use, e.g., when shearing forces occur during transplantation. The separation of the cells and the immune system is then no longer ensured. Rejection reactions may occur.

Another disadvantage of the known device is based on the restriction of its function to production of crosslinked microcapsules. Other geometric forms of crosslinked substances cannot be achieved with the single droplet principle.

The object of the present invention is to improve upon the known device described above for production of microcapsules, whereby the most homogeneous possible crosslinking of a crosslinkable substance and an expanded range of applications are the goals. The object of the invention is also to provide an improved method for producing crosslinked substances, e.g., microcapsules which are characterized in particular by an improved biological or medical usability. Finally, the object of this invention is also to create improved crosslinked substances such as microcapsules or other shaped bodies or layers.

The objects are achieved by a method having the features according to Patent Claim 1. Advantageous embodiments and applications of this invention are derived from the dependent claims.

This invention includes the general technical teaching, based on the device and the process, namely applying the crosslinking agent with a jet of the crosslinking agent which is directed at a substance that is initially uncrosslinked or pre-crosslinked (in general also: capsule substance). The uncrosslinked substance is mixed with the crosslinking agent e.g. as a jet in the form of micro-droplets, a filament or a layer, or as an uncrosslinked layer of the crosslinkable substance on a carrier. The pre-crosslinked (not yet completely crosslinked) substance is crosslinked, for example, by a first crosslinking of the crosslinkable substance with the jet of the crosslinking agent or in a precipitation bath before it is subjected to another crosslinking with another jet of the crosslinking agent. The invention permits in general the use of shaped articles which are adapted to the respective application and preferably include microcapsules, molded bodies, e.g., for implantation purposes or layers.

Preferably the jet of the crosslinking agent is so fast that the crosslinking agent penetrates into the uncrosslinked or not yet completely crosslinked substance, e.g., microcapsules. This offers the advantage that the crosslinking process is not limited to the regions of the crosslinkable substance near the surface, e.g., the surface of microcapsules or layers on substrates but instead also includes the interior of the microcapsules or layers.

In addition, it is preferably also provided that the jet of the crosslinking agent is so slow that the crosslinking agent does not come out again after penetrating into the uncrosslinked or not yet completely crosslinked substance. This is advantageous because the crosslinking agent can no longer contribute toward crosslinking after it escapes from the substance.

The jet speed, which conforms to the two boundary conditions mentioned above, may be determined easily through experiments by investigating the degree of crosslinking achieved in the crosslinkable substance for various jet speed values. One available test method is in particular a confocal microscopic imaging of the crosslinked material, e.g., for detection of the crosslinking and/or detection of precipitated metal residues. The speed of the jet of the crosslinking agent can then be adjusted easily by varying the pressure on the particle jet, with pressures between 1 bar and 2 bar being very suitable.

It is advantageous here that the crosslinking agent on penetration into the initially uncrosslinked or not yet completely crosslinked substance, causes injection channels to be formed which promote the crosslinking in the interior of the material. The injection channels may remain at least partially even in the crosslinked state of the substance, in particular in the case of highly viscous alginates (e.g., 40 mPa·s$^{-1}$ or higher) and thereby optionally promote diffusion of an active ingredient to the outside through the injection channels. This reduces the diffusion inhibition of the capsules. This is important for applications in the release of active ingredients in particular when larger molecules are encapsulated such as antibodies or factor VIII or fragments of this factor.

As an alternative, the crosslinking conditions may be selected so that the permeability of the crosslinked material e.g. for the nutrient exchange or oxygen exchange for the release of therapeutic factors is reduced or e.g. for the immunological isolation of the encapsulated material it may even be suppressed completely. For example, in the case of crosslinking of alginates, the permeability can be adjusted through the concentration of the crosslinkable starting solution (alginate solution) and/or through a layered design of the capsules. In crosslinking alginate with barium particles, an alginate concentration of 0.7% (w/v) is preferably established. At a lower concentration of 0.65% (w/v), for example, the permeability that is established permits substances having a molecular weight of approximately 9000 kDA to pass through. A layered structure of the capsules may include, for example, crosslinking with calcium on the inside and crosslinking with barium on the outside, so that the permeability on the inside is greater than that on the outside.

The term "active ingredient" is understood here in general terms and includes, for example, individual cells, cell groups or cell constituents, human or animal tissue or medically active substances such as pharmaceutical substances or hormones.

In addition, in a preferred embodiment of the invention, a nozzle arrangement is provided to promote the formation of droplets or the formation of capsules as the dispensing device, said nozzle arrangement blowing a shape-imparting jet against the jet of the capsule substance. Preferably, the shape-imparting jet here surrounds the jet of the capsule substance, for example, coaxially. As an alternative, this invention may also be implemented with other essentially known dispensing devices for forming droplets, jets or layers.

In a variant of this invention, the jet of the crosslinking agent runs essentially at a right angle to the jet of the capsule substance. The jet of the capsule substance preferably runs essentially at a right angle from top to bottom (vertically), whereby the dispensing device for the jet of the crosslinking agent is arranged laterally next to the jet of the capsule substance. However, the jet of the capsule substance may also be at any angle from 0° to 90° to the vertical.

The jet of the crosslinking agent preferably has a jet widening angle between 10° and 170° in the vertical and/or horizontal direction(s), but other values are also possible. A jet widening angle between 10° and 30° has proven to be especially advantageous. The optimal jet widening value, however, depends on the device used and should be selected so that on the one hand the kinetic energy of the crosslinking agent dispensed is reduced as little as possible due to the widening of the jet and on the other hand the jet of as yet uncrosslinked microcapsules is in adequate contact with the jet of the crosslinking agent.

In another variant of the invention, however, the dispensing device for the jet of the crosslinking agent is in the form of a ring and surrounds the jet of the capsule substance. The jet of the crosslinking agent here runs preferably radially from the outside to the inside, whereby the jet of the crosslinking agent preferably has a predetermined oncoming flow angle with respect to the jet of the capsule substance.

The oncoming flow angle of the jet of the crosslinking agent with respect to the jet of the capsule substance may assume any values in the range between 0° and 90°, but values of more than 15° have proven to be especially advantageous.

In the case of a ring-shaped dispensing device for the jet of the crosslinking agent, several outlet nozzles are preferably distributed over the circumference of the dispensing device, so that the crosslinking agent strikes the jet of the capsule substance from various sides, thus permitting an optimum effect of the crosslinking agent on the capsule substance.

In another variant of the invention the dispensing device for the capsule substance, the dispensing device for the crosslinking agent and the nozzle arrangement for the shape-imparting jet have mutually adjacent outlet openings. For example it is possible for the capsule substance to be dispensed through a central nozzle, which is surrounded by a coaxial nozzle for the shape-imparting jet, while the crosslinking agent is dispensed through a nozzle which is also coaxial and is situated on the outside of the former. The jet of the crosslinking agent preferably runs here essentially coaxially with the jet of the capsule substance, in which case the jet of the crosslinking agent preferably surrounds the jet of the capsule substance.

In a preferred embodiment of this invention, the crosslinking device and/or the dispensing device for the capsule substance is/are preferably operated with compressed air. For example a crosslinking agent may be dispensed through particle flow devices which are known from dental technology such as the Dentatech Prophy AP II, Dentatech Selector AP or Kavo Prophyflex 5.

Furthermore there is the possibility that for further improvement in the crosslinking of the microcapsules, a precipitating bath may be provided additionally, likewise containing crosslinking agents. The precipitation bath should be large enough as a measure for secondary crosslinking so that the jet of the capsule substance does in fact enter the precipitation bath because the jet with the crosslinking agent may lead to a lateral deflection of the crosslinking agent. As an alternative, the precipitation bath may be provided as a measure, for pre-crosslinking. Pre-crosslinked material (e.g., capsules) can be removed from the precipitation bath, arranged on a solid substrate, for example, and subjected to a post-crosslinking with a jet of the crosslinking agent.

Alternative embodiments of the inventive device are directed at providing at least one additional dispensing device and crosslinking of layers, e.g., on substrates. Due to the use of two or more dispensing devices, in addition to said crosslinking agent, at least one other crosslinking agent, active ingredients, alginate powder or crystals or biological substances may be shot into the volume of the crosslinkable substance to advantage. Thus the possible applications of crosslinkable substances, in particular crosslinkable biopolymers such as alginates, are increased substantially.

A preferred application of the invention consists of encapsulation of biologically or medically active cells (i.e., including transformed cells) in ionotropic gels, e.g., alginates. In this application, the rate of the crosslinking agent supplied is selected so that the incorporated cells are not damaged by the jet of the crosslinking agent. A speed limit is selected through experiments in particular as a function of the particles of the crosslinking agent used.

In addition, the inventive encapsulation method and/or the respective device may also be used in biotechnology processes in which immobilized cells, (e.g., microorganisms, animal cells, yeast cells and plant cells as well as plant protoplasts) are used for production and secretion of active ingredients, amino acids, primary and secondary metabolites.

In addition the invention may also be used as already indicated previously for so-called "controlled drug release" in organisms (in particular animals or humans), whereby a therapeutically active substance is enclosed in the cell. The permeability of the microcapsules for the substance is adjusted so that the substance is released in a controlled manner after implantation of the microcapsules. The therapeutically active substance here may also be enclosed in so-called liposomes (lipid vesicles) and then encapsulated. Advantageously, the following applications of alginates crosslinked according to this invention may also be implemented to advantage in the release of active ingredients.

To combat tumors (e.g., in the brain), endostatin or human monoclonal antibodies (mol. wt. 60.000 kDA or more) may be embedded in microcapsules and the permeability may be adjusted so that the active ingredients are released slowly, depending on requirements. The permeability is adjusted, for example, through the concentration of the alginate solution (see above) and through the choice of the crosslinking agent and/or the amount of crosslinking agent.

Contrast media such as gadolinium derivatives (in particular Magnavist, registered trademark) may be embedded in microcapsules crosslinked according to this invention for diagnostic purposes, e.g., in NMR imaging. This makes it possible to prevent in an advantageous manner a slow release from being achieved in deviation from a rapid degradation and secretion through the kidneys with traditional contrast media. Other applications involve the embedding of medication, e.g., antibodies or magnetic particles.

The preferred crosslinkable substance to be used according to the invention is an alginate. A solution of a highly viscous alginate is preferably used. The viscosity is preferably greater than 15 mPa·s. As an alternative, alginate having a lower viscosity (up to approximately 1 to 5 mPa·s) may be used, in which case the concentration of the alginate is preferably adjusted to approximately 2% to 3% (w/v).

As an additional general technical teaching with regard to the device and method, this invention includes the fact that an essentially conventional crosslinking of the crosslinkable substance (e.g., microcapsules) is performed first in a precipitation bath containing a crosslinking agent. Then the crosslinked material is separated from the precipitation bath (e.g., removed from the precipitation bath) and placed on a fixed substrate where it is subjected to further crosslinking or some other modification with a jet of at least one additional crosslinking agent, active ingredients, powder or crystals or crosslinkable substance (e.g., alginate powder or crystals) or biological substances in the volume of the substance which is crosslinked in the precipitation bath.

Figure 2:
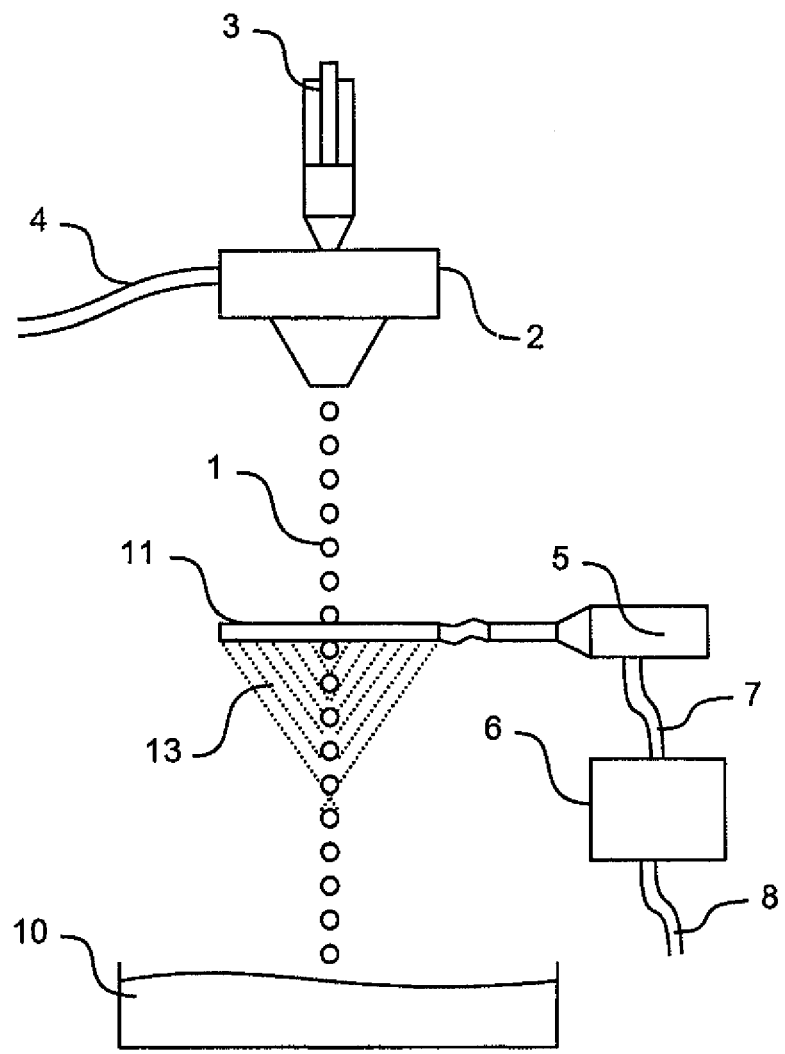
Figure 3:
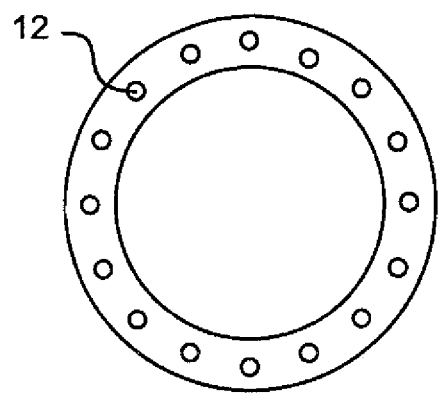
Figure 5:
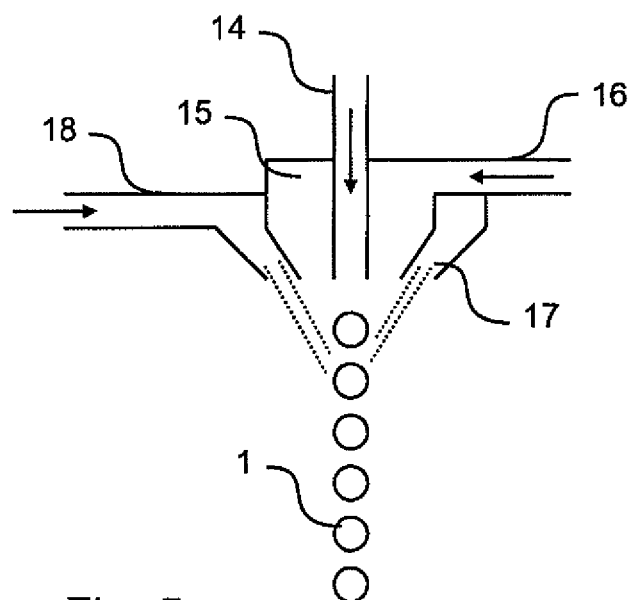
Figure 4:
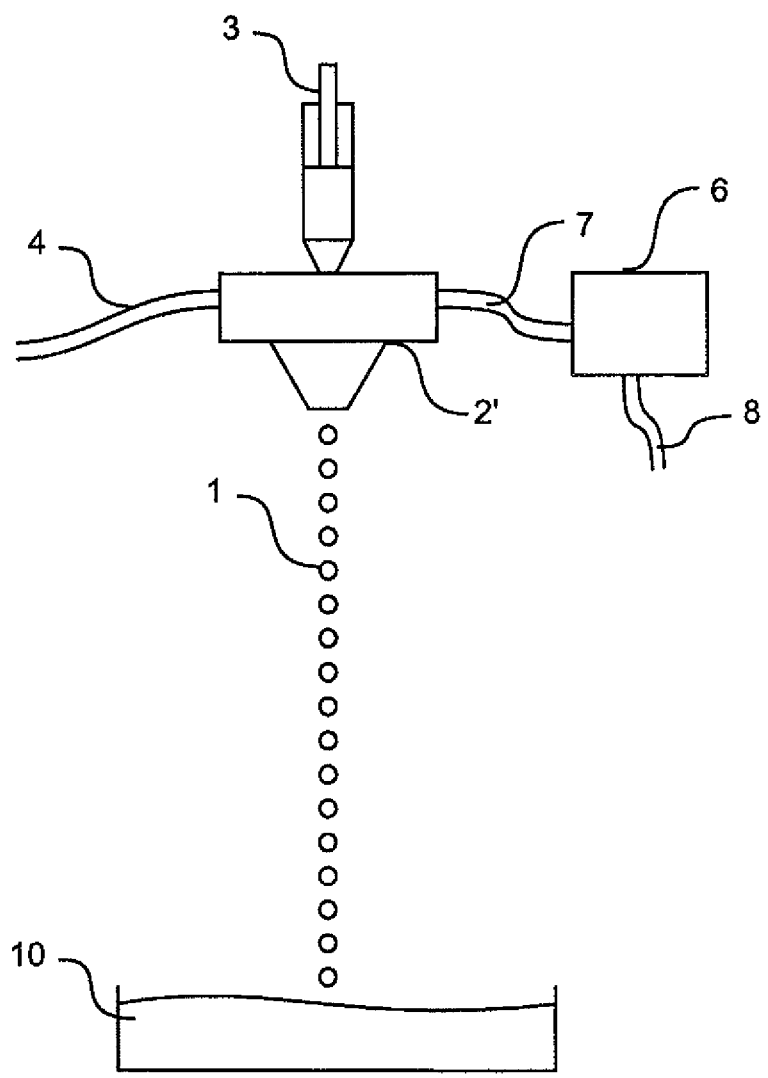
Figure 6:
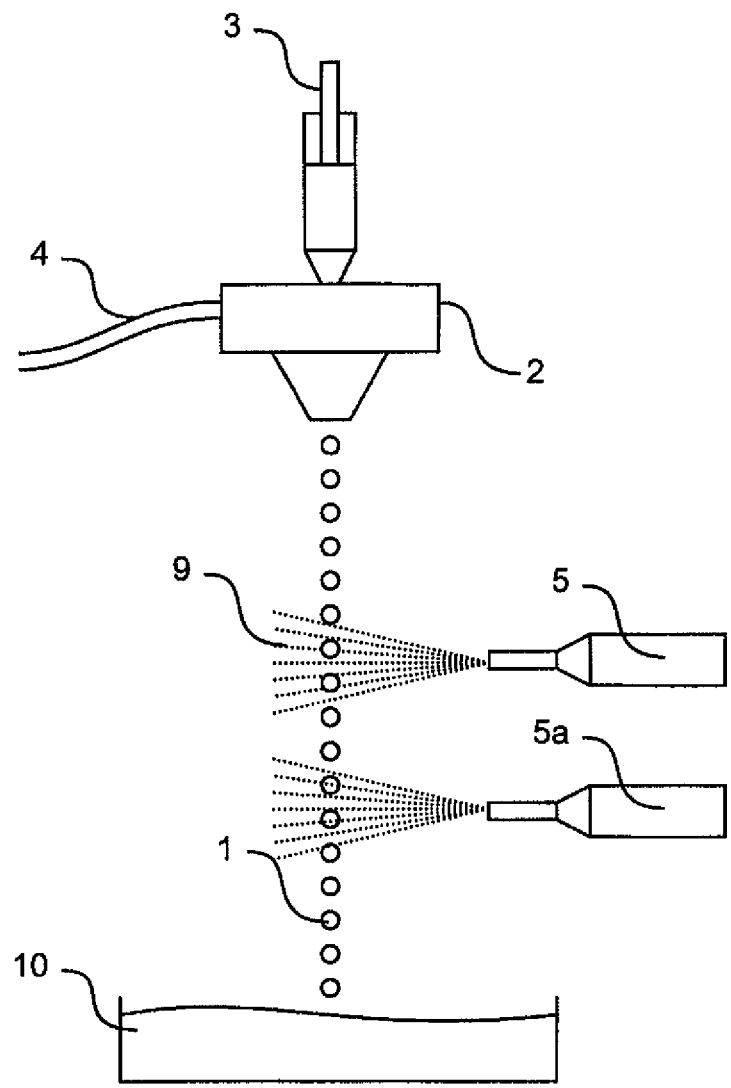
Figure 7:
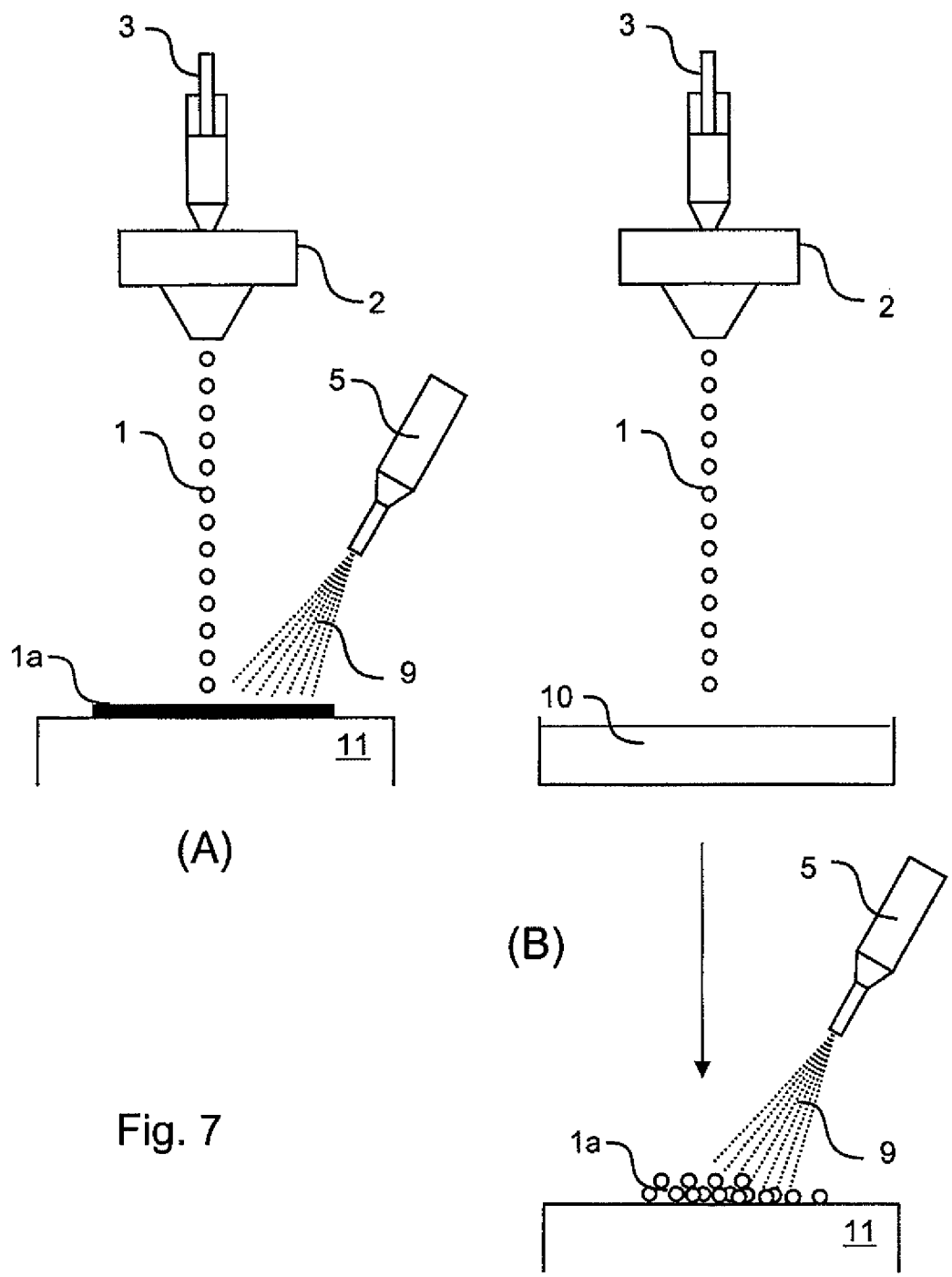

Other advantageous refinements of this invention are characterized in the subclaims or they are explained in greater detail below together with the description of the preferred exemplary embodiments on the basis of the figures, which show:

FIG. 1 an inventive device for producing biological microcapsules from alginates, whereby an alginate jet comes in contact laterally with a jet of crosslinking agent, FIG. 2 an alternative embodiment of such a device in which the alginate jet comes in contact with the crosslinking agent through a ring-shaped nozzle arrangement, FIG. 3 a detailed view of the ring-shaped nozzle arrangement from FIG. 2, FIG. 4 an alternative embodiment of such a device in which the outlet openings for the alginate, the fan air and the crosslinking agent are arranged in direct mutual proximity, FIG. 5 a detailed view of the nozzle arrangement of the device according to FIG. 4, FIG. 6 a modified embodiment of an inventive device for producing biological microcapsules from alginates, and FIG. 7 additional embodiments of the inventive device for producing crosslinked alginates.

The inventive device depicted in FIG. 1 is used to produce biological microcapsules 1 of crosslinkable alginates, whereby the microcapsules 1 contain various biological active ingredients (e.g., cells, tissue, biologically or medicinally active substances such as hormones). The enveloping of the biological active ingredients in the microcapsules 1 offers the advantage that they are not rejected by the endogenous immune system after being incorporated because the material of the microcapsules 1 is biocompatible.

The inventive device has as the first dispensing device an encapsulation nozzle 2 which receives a liquid mixture of alginates and the biological active ingredients that are to be administered, said mixture being supplied via a plunger 3, whereby the encapsulation nozzle 2 is also connected to a compressed air line 4.

However, it is also possible for the mixture of alginates and the active ingredients to be administered is supplied to the encapsulation nozzle 2 through a conventional disposable syringe. As an alternative, the first dispensing device may be one of the devices for producing droplets under the influence of electric fields such as those described, for example, in the book by W. M. Kuehtreiber et al. (eds.) "Cell encapsulation technology and therapeutics" (Birkhaeuser, Boston).

The mixture is then blown on by a coaxial air jet to form the microcapsules 1 so that the encapsulation nozzle 2 dispenses a jet of droplets of microcapsules 1.

The encapsulation nozzle 2 is arranged here in such a way that the jet of microcapsules 1 is directed essentially vertically downward from top to bottom.

At the side next to the jet of the microcapsules 1, a particle jet device 5 is arranged as the second dispensing device which receives a crosslinking agent under pressure from a base unit 6 through a line 7.

With regard to the crosslinking agent that can be used, reference is made to the aforementioned publication "Microencapsulation-Based Cell Therapy" as well as German Patent application 199 35 231, so that a detailed description of the numerous possible crosslinking agents may be omitted here.

The base unit 6 for the particle jet device 5 is connected to a compressed air source (not shown for the sake of simplicity) by a compressed air line 8.

The particle jet device 5 may be, for example, a Dentatech Prophy AP II, a Dentatech Selector AP or a Kavo Prophyflex 5, all of which are devices known from dental medical technology.

In this exemplary embodiment of the inventive device, the particle jet device 5 delivers a jet 9 of the crosslinking agent, whereby the jet 9 of the crosslinking agent has a jet widening angle of approximately 30° in both the vertical direction and in the horizontal direction to achieve adequate crosslinking of the microcapsules 1.

The speed of the particles of the jet 9 is so great here that the individual particles of the crosslinking agent penetrate into the microcapsules 1 that are not yet crosslinked so that the crosslinking process is not limited to the areas of the microcapsules 1 near the surface but instead also includes the interior of the microcapsules 1.

However, the speed of the particles of the jet 9 is not so great that the individual particles of the jet 9 leave the microcapsules 1 again after penetrating into them because that would impair the crosslinking process or it might damage cells in the microcapsules.

The jet 9 of the crosslinking agent is preferably composed of a discontinuous jet of particles of the crosslinking agent. Depending on the operating principle of the particle jet device, the particles may have atomic or microscopic dimensions. The particle jet device 5 preferably dispenses liquid, suspended or solid particles having a characteristic size in the range of 500 nm to 100 μm. For example, there is the possibility of the particle jet device 5 dispensing a liquid crosslinking solution (e.g., 20 mM Ba or Cl solution). It is also especially advantageous if the crosslinking solution is enclosed in lipid vesicles which are then enclosed in the alginate beads. With an increase in temperature, the lipid membrane then becomes permeable and the divalent cations are released.

Finally, a conventional precipitation bath is also arranged beneath the encapsulation nozzle 2; the precipitation bath also contains crosslinking agent and therefore can lead to an improvement in the crosslinking of the microcapsules 1. Such precipitation baths are known from the two publications mentioned above, so that no detailed description of precipitation baths need be given here.

The design and/or operation of the encapsulation nozzle 2 is/are selected according to FIG. 1, for example, such that the jet of crosslinkable substance (alginate) consists of a plurality of microdroplets. This invention is not limited to the crosslinking of microdroplets, and instead the encapsulation nozzle 2 may be operated or designed so that other jet forms can be produced. For example, at a different operating pressure, the subdivision of the jet into microdroplets can be cancelled and instead a continuous alginate filament may be produced. The alginate filament may have a cross-sectional shape which depends on the shape of the encapsulation nozzle 2. For example, the alginate filament may be formed with a circular cross section (diameter in the range of 50 μm to 5 mm or more, for example). This design permits the production of cylindrical alginate bodies which are of interest as implant bodies, for example. As an alternative, the nozzle may also be in the form of a slot. In this case the jet of alginate solution forms a layer-like liquid curtain which is crosslinked according to the principles explained above. Depending on the shape of the encapsulation nozzle, other layer forms may be produced, e.g., curved layers. The formation of crosslinked alginate layers on substrates is explained below with reference to FIG. 7.

The embodiment of an inventive device depicted in FIG. 2 largely corresponds to the exemplary embodiment described above and depicted in FIG. 1 so that the same reference notation is used below for corresponding components and to avoid repetition, reference is made essentially to the description given above for FIG. 1.

The particular feature of this embodiment is essentially that the particle jet device 5 is connected to a ring-shaped nozzle arrangement 11 which is shown in detail in FIG. 3.

The nozzle arrangement 11 surrounds the jet of microcapsules 1 in the form of a ring and has numerous nozzle openings 12 distributed around its circumference, emitting a fan-shaped jet 13 of the crosslinking agent. The jet 13 of the crosslinking agent here has an oncoming flow angle of approximately 40° in comparison with the jet of microcapsules 1 and otherwise runs radially inward so that the jet 13 of the crosslinking agent strikes the microcapsules 1.

Here again, the speed of the jet 13 is so great that the crosslinking agent penetrates into the individual microcapsules 1 but not so slowly that the crosslinking agent does not then escape again.

Finally, the embodiment of an inventive device depicted in FIG. 4 also corresponds largely to the exemplary embodiment described above and depicted in FIG. 1 so that the same reference notation is also used below for corresponding components and reference is made to the preceding description to avoid repetition.

The particular feature of this exemplary embodiment consists of the structural design of an encapsulation nozzle 2', which is shown in detail in FIG. 5.

Thus the encapsulation nozzle 2' has a central nozzle 14 for dispensing the alginate-cell mixture, whereby the nozzle 14 is surrounded by a concentric nozzle 15 which is supplied with compressed air through a feeder line 16. The compressed air escaping from the nozzle 15 here promotes the formation of fine droplets of the alginate-cell mixture coming out of the nozzle 14. The nozzle 15 may be designed and/or operated accordingly to form other jet forms.

Finally, the nozzle 15 is surrounded by a nozzle 17 which is also in the form of a ring and receives the crosslinking agent through a feeder line 18. The crosslinking agent comes out of the nozzle 17, with the emerging jet of the crosslinking agent also having a radial component in addition to the axial velocity component and therefore striking the individual microcapsules 1, which results in their crosslinking.

The speed of the jet of crosslinking agent emerging from the nozzle 17 is again so great that the crosslinking agent penetrates into the individual microcapsules 1 without leaving them again.

FIG. 6 illustrates a modified embodiment of this invention in which in addition to the dispensing device 5 described above for dispensing the crosslinking agent, at least one other dispensing device 5a is provided along the falling zone of the alginate droplets. The dispensing device 5a is preferably constructed like the dispensing device 5 described above. Due to the use of multiple dispensing devices, the following novel applications can be implemented in the production of encapsulated or layered alginate material.

The various dispensing devices 5, 5a may inject various crosslinking agents into the alginate at various speeds so that different areas in the alginate are crosslinked with different ions. For example, calcium chloride may be dispensed at a high speed through the first dispensing device 5 so that calcium crosslinking takes place in the core of the capsules 1, whereas barium chloride crystals are dispensed in the second dispensing device 5a. The speed of the barium chloride crystals is adjusted so that they reach only the outer layers of the alginate. Production of microcapsules crosslinked with calcium on the inside and with barium on the outside and having biological materials enclosed in them (e.g., cells, tissue) has the advantage that the essential physiologically active calcium is present in the environment of the biological materials, whereas barium prevails in the areas near the surface and has a greater crosslinking stability. Another advantage is the influence on the permeability of the microcapsules. Diffusion is greater in the interior of the microcapsules than in the periphery where crosslinking is performed with barium.

Furthermore, the additional dispensing device 5a may be provided for injection of biological factors. For example, mesenchymal stem cells may be encapsulated, with barium crosslinking being performed first and then an injection of growth hormones in solid form being performed next. As an alternative, therapeutic factors (active ingredients) may also be enclosed in the crosslinked alginates on the additional dispensing device 5a.

Another application of the additional dispensing device 5a consists of supplying alginate powder or crystals. In this embodiment, the local alginate concentration in the microcapsules or the otherwise shaped alginate body may be varied. Alginate compositions consisting of a locally defined mixing ratio of different alginates can be produced. Such alginate compositions form composite materials having novel physical and chemical properties, which are manifested in particular in novel release kinetics of therapeutic factors from cells and tissues or in "controlled drug release."

Finally, it is also possible with the additional dispensing device 5a to inject other hydrogels or hydrophobic polymer microparticles. In the latter case, microdomains may be created as a reservoir for hydrophobic (lipid-soluble) factors within the crosslinked material. Furthermore thermotropic hydrogels (e.g., agarose) may also be injected. This has the advantage that the release genetics [sic; kinetics] of the microcapsules can be accelerated by local heating (microwave therapy). Finally, the active ingredient may also be released toward the interior in order, for example, to trigger encapsulated cells biochemically over a period of time.

It is also possible to incorporate sugar, which alters the water structure and thus alters the permeability of the capsules at various temperatures. Applications in food technology, for example, coloring agents may be added to impart color to the alginates.

FIG. 7A, B illustrates other modifications of the invention in which the capsule substance in a crosslinked or uncrosslinked state on a substrate is subjected to further crosslinking and/or modification. According to FIG. 7A, the microdroplets 1, e.g., of dissolved alginate strike the surface of a substrate 11 on which the alginate solution forms a layer 1a. The dispensing device 5 is in this case directed against the layer 1a to produce crosslinked substances bound to the substrate. In deviation from the illustration, the surface of the substrate 11 may be designed with a curvature. The crosslinked alginate layer is formed with the curvature accordingly.

The design according to FIG. 7A may be used in particular as part of nanotechnology. The crosslinking of the crosslinkable substance is performed to form a protective coat and/or a substrate system for technical devices having characteristic dimensions in the μm to nm range. Active ingredients as consumable substances may also be enclosed in nanotechnological devices (inclusion of energy devices).

According to FIG. 7B, the microdroplets are first crosslinked in a precipitation bath by an essentially known method. Then the crosslinked capsules 1a are arranged in a layer on a substrate 11, where they are subjected to further crosslinking and/or modification according to the principles explained above using the dispensing device 5. The crosslinked capsules 1a can be separated from the precipitation bath, for example, by filtering out the crosslinked capsules 1a or by draining out the precipitation bath. In addition a pre-crosslinking may be provided according to FIG. 1.

This invention is not limited to the preferred embodiments described above. Instead, a plurality of variants, combinations and modifications making use of the inventive idea are possible, and therefore fall within the scope of protection.

The invention claimed is:

1. A method of producing a crosslinked substance from a crosslinkable capsule substance, comprising the steps of:
    generating a jet of the crosslinkable capsule substance;
    directing at least one jet of a crosslinking agent to the jet of the crosslinkable capsule substance for crosslinking the capsule substance, wherein the speed of the jet of the crosslinking agent is fast enough that the crosslinking agent penetrates into a core of uncrosslinked capsule substance; and
    forming at least one of the jet of the capsule substance and the jet of crosslinking agent by blowing one or both of the capsule substance and the crosslinking agent using compressed air;
    wherein the capsule substance contains crosslinkable alginates.

2. The method according to claim 1, further comprising the step of directing at least another jet of the crosslinking agent, an active ingredient, or an additive to the jet of the crosslinkable capsule substance.

3. The method according to claim 1, wherein the speed of the jet of the crosslinking agent is slow enough that the crosslinking agent remains with the capsule substance after penetrating into the uncrosslinked capsule substance.

4. The method according to claim 1, further comprising shaping the jet by using at least one of an encapsulation nozzle and a nozzle arrangement for blowing a shape-imparting jet against the jet of the capsule substance, whereby the shape-imparting jet surrounds the jet of the capsule substance.

5. The method according to claim 4, wherein at least one of the encapsulation nozzle and the nozzle arrangement is configured for forming a jet that is subdivided into microdroplets at a continuous jet.

6. The method according to claim 4, wherein at least one of the encapsulation nozzle and the nozzle arrangement is configured to form a continuous jet with a predetermined diameter or to form layers.

7. The method according to claim 4, further comprising dispensing at least two of the jet of the crosslinkable capsule substance, the jet of crosslinking agent, and the shape-imparting jet from mutually adjacent outlet openings.

8. The method according to claim 7, further comprising dispensing the jet of the crosslinking agent essentially coaxially with the jet of the capsule substance.

9. The method according to claim 8, further comprising surrounding the jet of the capsule substance with the jet of the crosslinking agent.

10. The method according to claim 1, further comprising directing the at least one jet of the crosslinking agent at an angle between 15° and 90° with respect to the jet of the capsule substance.

11. The method according to claim 1, further comprising dispensing the at least one jet of the crosslinking agent in the form of a ring that surrounds the jet of the capsule substance.

12. The method according to claim 11, wherein the at least one jet of the crosslinking agent has a predetermined oncoming flow angle with respect to the jet of the capsule substance and otherwise runs radially toward the interior of the ring.

13. The method according to claim 11, further comprising dispensing the at least one jet of the crosslinking agent from multiple outlet nozzles which are arranged so as to be distributed over the circumference of the ring.

14. The method according to claim 1, wherein the jet of the capsule substance has a free length of between 5 cm and 80 cm before contacting the jet of the crosslinking agent.

15. The method according to claim 1, further comprising:
    directing the jet of the capsule substance in an essentially vertically downward direction; and providing a collecting basin essentially below the jet of the capsule substance, the collecting basin containing a crosslinking agent.

16. The method according to claim 15, further comprising providing a substrate to accommodate the capsule substance which is crosslinked in the collecting basin and directing the at least one jet of the crosslinking agent, or an additional substance, at the capsule substance on the substrate, 17. The method according to claim 1, further comprising:
directing the jet of the capsule substance in an essentially vertically downward direction;
providing a substrate essentially below the jet of the capsule substance; and
directing the jet of the crosslinking agent to a surface to the substrate.

18. The method according to claim 1, wherein the crosslinking agent contains free or dissolved ions or salt crystals.

19. The method according to claim 1, wherein the jet of the crosslinking agent contains particles of the crosslinking agent in liquid, suspended, or solid form.

20. The method according to claim 1, wherein the jet of the crosslinking agent contains crosslinking agent capsules which contain and sheath the crosslinking agent.

21. The method according to claim 20, wherein the crosslinking agent capsules are lipid vesicles.

* * * * *